United States Patent
Cheng et al.

(10) Patent No.: US 11,873,318 B2
(45) Date of Patent: Jan. 16, 2024

(54) COMPOSITIONS COMPRISING DICHLOROACETIC ACID, PROCESSES FOR PREPARING SAME AND USES THEREOF

(71) Applicants: CHANGZHOU SYNTHEALL PHARMACEUTICALS CO., LTD., Jiangsu (CN); SHANGHAI STA PHARMACEUTICAL R&D CO., LTD., Shanghai (CN)

(72) Inventors: Hu Cheng, Jiangsu (CN); Chenchen Hu, Shanghai (CN); Jiaxin Song, Jiangsu (CN); Yang Liu, Jiangsu (CN); Tingting Qian, Jiangsu (CN); Xianzhe Wang, Jiangsu (CN); Jimin Yang, Jiangsu (CN)

(73) Assignees: CHANGZHOU SYNTHEALL PHARMACEUTICALS CO., LTD., Changzhou (CN); SHANGHAI STA PHARMACEUTICAL R&D CO., LTD., Shanghai (CN)

( * ) Notice: Subject to any disclaimer, the term of this patent is extended or adjusted under 35 U.S.C. 154(b) by 0 days.

(21) Appl. No.: 17/870,551

(22) Filed: Jul. 21, 2022

(65) Prior Publication Data

US 2023/0002438 A1    Jan. 5, 2023

Related U.S. Application Data

(63) Continuation of application No. PCT/CN2021/095036, filed on May 21, 2021.

(51) Int. Cl.
    *C07H 21/00*      (2006.01)
(52) U.S. Cl.
    CPC .................... *C07H 21/00* (2013.01)
(58) Field of Classification Search
    CPC .......... C07H 1/00; C07H 21/00; G01N 30/88; C07C 51/487
See application file for complete search history.

(56) References Cited

U.S. PATENT DOCUMENTS

| | | | |
|---|---|---|---|
| 5,714,597 A | † | 2/1998 | Ravikumar |
| 2002/0119483 A1 | | 8/2002 | Wheeler et al. |
| 2005/0075490 A1 | | 4/2005 | Krotz et al. |

FOREIGN PATENT DOCUMENTS

WO      03085136 A1 † 10/2003

OTHER PUBLICATIONS

Abdulwahed et al., Intl. J. of Analytical Chemistry Article No. 5417549 : 9 pages (Mar. 2020). (Year: 2020).*
Kissling et al. Toxicological Sciences 107(1) :19-26 (Year: 2009).*
Kramer et al., Analytical Chemistry 31(2) : 250 (Year: 1959).*
Lui et al., Analytical Biochemistry 38:202 (Year: 1970).*
McFadden et al., Analytical Biochemistry 1:240 (Year: 1960).*
Mentasti, E., J. of Chromatography 417: 253 (Year: 1987).*
Petrarulo et al., J. of Chromatography 432:37 (Year: 1988).*
Notification of Transmittal of the International Search Report and Written Opinion for parent Application No. PCT/CN2021/095036, dated Aug. 25, 2021, 11 pages.
IARC Working Group "IARC monographs on the evaluation of carcinogenic risks to humans, dry cleaning, some chlorinated slovents and other industrial chemicals" *Dichloroacetic acid*, vol. 6, Feb. 14, 1995 (Feb. 14, 1995), ISSN: 0250-9555, 12 pages.
Lifongo, L.L.et al. "Thermal degradation of haloacetic acids in water", International Journal of the Physical Sciences vol. 5(6), pp. 738-747, Jun. 2010.
International Agency for Research on Cancer (IARC) Monograph "Dry Cleaning, Some Chlorinated Solvents and Other Industrial Chemicals" (IARC Monographs on the Evaluation of Carcinogenic Risks to Humans vol. 63).†

\* cited by examiner
† cited by third party

*Primary Examiner* — Ethan C Whisenant
(74) *Attorney, Agent, or Firm* — NIXON & VANDERHYE, P.C.

(57) ABSTRACT

Disclosed is a composition comprising dichloroacetic acid, a process for preparing the same and a use thereof. It has been discovered that the novel impurity is glyoxylic acid, and glyoxylic acid in dichloroacetic acid can be detected and its concentration accurately measured, by ion chromatography method.

20 Claims, 4 Drawing Sheets

Specification includes a Sequence Listing.

COMPOSITIONS COMPRISING DICHLOROACETIC ACID, PROCESSES FOR PREPARING SAME AND USES THEREOF

CROSS REFERENCE TO RELATED APPLICATIONS

This present application is a U.S. Continuation of International Application No. PCT/CN2021/095036 filed May 21, 2021 which designated the U.S. and claims priority of International application PCT/CN2020/091643 filed May 21, 2020, the entire contents of each of which are hereby incorporated by reference in their entireties.

REFERENCE TO SEQUENCE LISTING SUBMITTED ELECTRONICALLY

The content of the electronically submitted sequence listing (6950_0015_Sequence_Listing.xml; Size: 4 kilobytes; and Date of Creation: Jul. 19, 2022) filed with the application is incorporated herein by reference in its entirety.

TECHNICAL FIELD

The present disclosure relates to a composition comprising dichloroacetic acid, a process for preparing the same and a use thereof.

BACKGROUND

One method for inhibiting specific gene expression is with the use of oligonucleotides, especially oligonucleotides which are complementary to a specific target messenger RNA (mRNA) sequence. Several oligonucleotides are undergoing clinic trials for such uses. Oligonucleotides can also serve as competitive inhibitors of transcription factors, which interact with double-stranded DNA during regulation of transcription, to modulate their actions.

Oligonucleotides and their analogs also have found uses in diagnostic tests, research reagents, and other laboratory procedures. The widespread use of such oligonucleotides has increased the demand for rapid, inexpensive and efficient procedures for their modification and synthesis.

DCA (dichloroacetic acid) is a commonly used reagent for deblocking nucleotides during oligonucleotide synthesis. Because the addition of new nucleosides involves the repeated use of DCA for deprotecting the 5'-hydroxy group, it is important that this reagent be as free as possible of contaminants which may propagate impurities and produce improper sequences of the target oligonucleotide. It has been discovered that the impurities in DCA which may cause the failure of oligonucleotide synthesis such as chloral hydrate and 2,2-dichloroacetic anhydride (DCAA).

SUMMARY OF THE PRESENT DISCLOSURE

Because of the repetitious use of DCA for the removal of the oligonucleotide protecting groups, it is critical that DCA be free of contaminants which may propagate impurities and produce improper sequences of the target oligonucleotide. It was discovered that the presence of glyoxylic acid in DCA can have a deleterious effect when such DCA is used for deprotection of an acid labile protecting group during oligonucleotide synthesis. It has been further discovered that glyoxylic acid in DCA can be detected and its concentration accurately measured, by ion chromatography method (IC method).

One object of the present disclosure is to provide a composition comprising DCA and glyoxylic acid, wherein, the content of glyoxylic acid is below 1000 ppm.

It is a further object of the present disclosure to provide a process for preparing the composition.

It is a further object of the present disclosure to provide a process for preparing oligonucleotides by using the composition.

It is a further object of the present disclosure to provide a method for detecting glyoxylic acid in a sample of DCA.

These, as well as other important objects, will be become apparent during the following detailed description.

DETAILED DESCRIPTION OF THE PRESENT DISCLOSURE

In a first aspect, the present disclosure provides a composition comprising DCA and glyoxylic acid, wherein the content of glyoxylic acid is below 1000 ppm.

In certain embodiments, the content of glyoxylic acid in the composition is below 950 ppm, 900 ppm, 800 ppm, 700 ppm, 600 ppm, 500 ppm, 400 ppm, 300 ppm, 200 ppm, 100 ppm, 50 ppm, 40 ppm, 30 ppm, 20 ppm, 10 ppm, 9 ppm, 8 ppm, 7 ppm, 6 ppm, 5 ppm, 4 ppm, 3.5 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.1 ppm, 1.05 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, the content of glyoxylic acid in the composition is below 500 ppm, 450 ppm, 400 ppm, 350 ppm, 300 ppm, 250 ppm, 200 ppm, 150 ppm, 100 ppm, 90 ppm, 80 ppm, 70 ppm, 60 ppm, 50 ppm, 40 ppm, 30 ppm, 20 ppm, 15 ppm, 12 ppm, 10 ppm, 9 ppm, 8 ppm, 7 ppm, 6 ppm, 5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, the content of glyoxylic acid in the composition is below 50 ppm, 45 ppm, 40 ppm, 35 ppm, 30 ppm, 25 ppm, 20 ppm, 15 ppm, 12 ppm, 10 ppm, 9 ppm, 8 ppm, 7 ppm, 6 ppm, 5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, the content of glyoxylic acid in the composition is below 15 ppm, 14.5 ppm, 14 ppm, 13.5 ppm, 13 ppm, 12.5 ppm, 12 ppm, 11.5 ppm, 11 ppm, 10.5 ppm, 10 ppm, 9.5 ppm, 9 ppm, 8.5 ppm, 8 ppm, 7.5 ppm, 7 ppm, 6.5 ppm, 6 ppm, 5.5 ppm, 5 ppm, 4.5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, in the composition, the content of DCA is greater than 50%, greater than 55%, greater than 60%, greater than 65%, greater than 70%, greater than 75%, greater than 80%, greater than 85%, greater than 90%, greater than 95%, greater than 98%, greater than 99%, greater than 99.5%, greater than 99.8%, for example 99.8153% (by weight, GC/IC area, or any combination thereof).

In certain embodiments, in the composition, the content of glyoxylic acid is >0, which means the content of glyoxylic is not 0 (in certain embodiments of the present disclosure, the content of glyoxylic acid is preferably >0.05 ppm, or >1 ppm).

In certain embodiments, in the composition, the content of the DCA and the glyoxylic acid are determined by, for example, IC method. The IC method is preferably as defined below. Preferably, the content of DCA is quantified by the area normalization method. Preferably, the glyoxylic acid is quantified by the external standard method.

In the external standard method, the method for preparing the standard curve comprising:

i) preparing glyoxylic acid standard working solutions with concentrations of 2.5 ppm, 5 ppm, 15 ppm, 20 ppm and 25 ppm, respectively; and ii) conducting ion chromatography analysis; the concentrations of glyoxylic acid series standard working solutions and the corresponding peak area of the response ion chromatogram are linearly regressed to get a standard curve.

In the external standard method, the conditions of the ion chromatography analysis are as described in the present disclosure. The concentrations of glyoxylic acid series standard working solutions and the corresponding peak area of the response ion chromatogram are as shown in Table 1.

TABLE 1

| GA Content(ppm) | peak area (µs*min) |
| --- | --- |
| 2.5 | 0.000035 |
| 5 | 0.000098 |
| 15 | 0.000420 |
| 20 | 0.000563 |
| 25 | 0.000694 |

The regression equation of the standard curve is: $y=0.00003x-0.00004$ ($R^2=0.99861$).

In certain embodiments, the composition as defined in the present disclosure is used to deblock nucleotides during oligonucleotide synthesis.

In a second aspect, the present disclosure provides a DCA reagent, wherein the content of glyoxylic acid is below 1000 ppm.

In certain embodiments, the content of glyoxylic acid in the DCA reagent is below 950 ppm, 900 ppm, 800 ppm, 700 ppm, 600 ppm, 500 ppm, 400 ppm, 300 ppm, 200 ppm, 100 ppm, 50 ppm, 40 ppm, 30 ppm, 20 ppm, 10 ppm, 9 ppm, 8 ppm, 7 ppm, 6 ppm, 5 ppm, 4 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.1 ppm, 1.05 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, the content of glyoxylic acid in the DCA reagent is below 500 ppm, 450 ppm, 400 ppm, 350 ppm, 300 ppm, 250 ppm, 200 ppm, 150 ppm, 100 ppm, 90 ppm, 80 ppm, 70 ppm, 60 ppm, 50 ppm, 40 ppm, 30 ppm, 20 ppm, 15 ppm, 12 ppm, 10 ppm, 9 ppm, 8 ppm, 7 ppm, 6 ppm, 5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, the content of glyoxylic acid in the DCA reagent is below 50 ppm, 45 ppm, 40 ppm, 35 ppm, 30 ppm, 25 ppm, 20 ppm, 15 ppm, 12 ppm, 10 ppm, 9 ppm, 8 ppm, 7 ppm, 6 ppm, 5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, the content of glyoxylic acid in the DCA reagent is below 15 ppm, 14.5 ppm, 14 ppm, 13.5 ppm, 13 ppm, 12.5 ppm, 12 ppm, 11.5 ppm, 11 ppm, 10.5 ppm, 10 ppm, 9.5 ppm, 9 ppm, 8.5 ppm, 8 ppm, 7.5 ppm, 7 ppm, 6.5 ppm, 6 ppm, 5.5 ppm, 5 ppm, 4.5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm.

In certain embodiments, the DCA reagent is essentially free of glyoxylic acid, particularly, such as free of glyoxylic acid or having no detectable amount of glyoxylic acid.

In certain embodiments, in the DCA reagent, the content of DCA is greater than 90% (e.g., greater than 95%, greater than 98%, greater than 99%, or greater than 99.5%, greater than 99.8%, for example 99.8153%), by weight, GC area, by IC method, or any combination thereof.

In a certain embodiment, in the DCA reagent, the content of glyoxylic acid is >0, which means the content of glyoxylic is not 0 (in certain embodiments of the present disclosure, the content of glyoxylic acid is preferably >0.05 ppm, or >1 ppm).

In certain embodiments, in the DCA reagent, the content of the DCA and the glyoxylic acid are determined by, for example, IC method. The IC method is preferably as defined below. Preferably, the content of DCA is quantified by the area normalization method. Preferably, the glyoxylic acid is quantified by the external standard method as described in the present disclosure.

In certain embodiments, the DCA reagent as defined in the present disclosure is used to deblock nucleotides during oligonucleotide synthesis. In a third aspect, the present disclosure provides a process for preparing the composition, comprising: mixing a DCA material having greater than 1000 ppm glyoxylic acid with a glyoxylic acid capture reagent.

In certain embodiments, the capture reagent may be physically combined with glyoxylic acid or may chemically reacted with glyoxylic acid, and the resulting product has no or little effect on oligonucleotide synthesis.

In certain embodiments, the capture reagent is selected from amino acids, chemicals having bifunctional or multifunctional groups, hydroxylamine compounds, reductants, and mixtures thereof.

In certain embodiments, the amino acids are common used amino acids, including but not limited to, cysteine, lysine, phenylalanine, and mixtures thereof.

In certain embodiments, the chemicals having bifunctional or multifunctional groups are common used chemicals having bifunctional or multifunctional groups, including but not limited to, dihydric alcohols, for example, (2R)-propane-1,2-diol.

In certain embodiments, the hydroxylamine compounds are common used hydroxylamine compounds, including but not limited to, hydroxylamine salts such as hydroxylamine hydrochloride.

In certain embodiments, the reductants are common used reductants, including but not limited to, silanes, for example, triethylsilane.

In certain embodiments, the amount of the capture reagent is selected according to the content of glyoxylic acid in the composition. For example, the molar ratio of the capture reagent to glyoxylic acid is ≥1, such as ≥2 or ≥5. In an embodiment, in order to save costs, the molar ratio of the capture reagent to glyoxylic acid is 1 to 10, such as 5.

The purpose of the mixing is to mix the DCA material with a capture reagent well. Therefore, in certain embodiments, the mixing time for the DCA material and the capture reagent is selected according to the content of glyoxylic acid in the system. For example, the mixing time is 12-36 hours (hrs). The temperature for the mixing is, for example, room temperature.

In certain embodiments, in the DCA material, the content of glyoxylic acid is, for example, >1100 pm, >1200 ppm, >1300 ppm, >1400 ppm, >1500 ppm, >1600 ppm, >1700 ppm, >1800 ppm, >1900 ppm, >2000 ppm, >2100 ppm, >2500 ppm, >2600 ppm (for example, 2142.7 ppm). In certain embodiments, in the DCA material, the content of glyoxylic acid will have adverse effect on oligonucleotide synthesis.

In certain embodiments, the process for preparing the composition further comprises distillation (e.g. vacuum distillation) after the DCA material and the capture reagent mixing well (e.g. by standing or stirring), to obtain the target product.

In certain embodiments, the resulting product has any one of the following properties:
(i) it is a solid (for example, crystalline); therefore, it isn't distilled out under DCA vacuum distillation conditions;
(ii) it is a liquid, provided that it isn't distilled out under DCA vacuum distillation conditions; or
(iii) it is a liquid, provided that although it is distilled under DCA vacuum distillation conditions, it is easily separated from DCA by fractional distillation or by other methods.

In a fourth aspect, the present disclosure provides a process for preparing the DCA reagent, which is the same as the process for preparing the composition as defined above.

In a fifth aspect, the present disclosure provides a process for preparing oligonucleotides, comprising using the composition or the DCA reagent as defined above as a deprotecting reagent.

In certain embodiments, the process for preparing oligonucleotides comprises contacting an oligonucleotide with the composition or the DCA reagent as defined above.

In certain embodiments, the oligonucleotide bears a blocking group.

Oligonucleotides

The basic subunit of an oligonucleotide, such as RNA or DNA is depicted below.

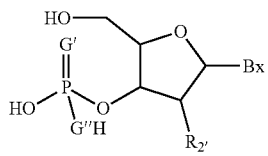

In an oligonucleotide, Bx serves as the Binding Member, the phosphate moiety [P(=G')(G"H)OH] serves as the Linking Member, and the residue, referred to as the sugar backbone, is the Backbone Member. The phosphate member forms covalent bonds by condensation with the 5'-OH of an adjacent subunit, thereby forming a phosphate diester bond. Where each of G' and G" is O, this is called a phosphodiester bond; where one of G' or G" is S and the other is O, this is called a phosphorothioate bond, and where both G' and G" are S, this is called a phosphorodithioate bond.

One skilled in the art will recognize that in naturally occurring nucleotides, $R_2'$ is H for DNA (deoxyribonucleic acid) and OH for RNA (ribonucleic acid), each of G' and G" is 0 and Bx is one of the following structures:

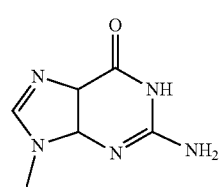

G

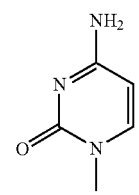

C

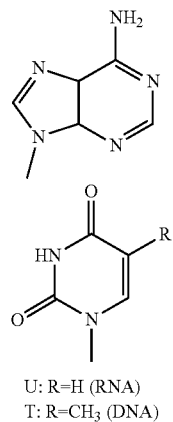

U: R=H (RNA)
T: R=CH₃ (DNA)

wherein G, C, A, U and T are guanine, cytosine, adenine, uracil and thymine, respectively.

In the above formula, G' and G" may be O or S, and $R_2'$ may be H, OH, or some other value.

In naturally occurring RNA, the binding member is a nucleosidic base selected from G, C, A and U, and the backbone comprises a sugar residue (ribosyl, i.e. $R_2'$ is OH) and a phosphate (G'=G"=O). The ribosyl sugar residue is the backbone member, while the phosphate joins adjacent monomers through the 5'- and 3'-oxygen atoms on the ribosyl ring. The sugar is covalently bound to the nucleosidic base at the 1'-position, the -β-D configuration predominating.

Naturally occurring DNA is analogous to RNA, except that the sugar is a 2'-deoxyribosyl ($R_2'$ is H).

Generally oligonucleotides according to the present disclosure include naturally occurring and non-naturally occurring oligonucleotides. In general, oligonucleotides according to the present disclosure include compounds of the formula (I):

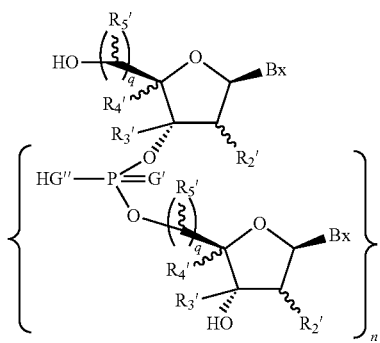

(I)

wherein each Bx is a nucleobase as defined herein, each q is 0 or 1, each of $R_2'$ is H or OH, reversibly-protected OH or a substituent or together with $R_4'$ forms a bridge; $R_3'$ is H or a substituent; $R_4'$ is H, a substituent or together with $R_2'$ or $R_5'$ forms a bridge; $R_5'$ is H, a substituted or together with $R_4'$ forms a bridge, and each squiggly bond ($\sim$) indicates that the bond may be in the up or down configuration.

The naturally occurring oligonucleotides are those in which each of Bx is selected from G, C, A, U (for RNA) and T (DNA), each of G' and G" is O, each $R_3'$, each $R_4'$, each $R_5'$ is H, each q is 1 and n is an integer, and the sugar oxygens are in the ribosyl configuration. Conversely, non-naturally occurring oligonucleotides include those in which at least one of following conditions applies: at least one Bx is a nucleobase other than a member selected G, C, A, U (for RNA) and T (DNA), at least one of the sugar oxygens is in other than the ribosyl configuration. As used herein, the term "oligonucleotides" and non-naturally occurring oligonucleotides, or mixtures thereof. In specific embodiments of the present disclosure, the term oligonucleotide having both naturally-occurring and non-naturally-occurring nucleotide subunits. In specific embodiments of the disclosure, one or more nucleobases, sugar backbones and/or phosphate linking members are non-naturally-occurring. These features will be described in greater detail below.

Sugar Backbone

In general, the sugar backbone has the structure:

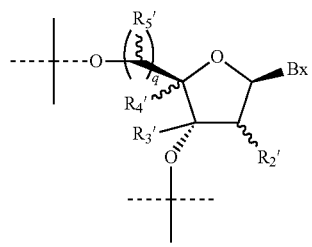

wherein each Bx is a nucleobase as defined herein, q is 0 or 1, each of $R_2'$ is H, OH, reversibly-protected OH or a substituent or together with $R_4'$ forms a bridge; $R_3'$ is H or a substituent; $R_4'$ is H, a substituent or together with $R_2'$ or $R_5'$ forms a bridge; $R_5'$ is H, a substituent or together with $R_4'$ forms a bridge. The dashes (---) indicate the positions at which the sugar moiety is bond to a phosphate linker to form a nucleotide bond.

The person skilled in the art will recognize that when $R_2'$ is in the down configuration and q is 1, the ring is a ribosyl ring, whereas when $R_2'$ is in the up configuration and q is 1, the ring is an arabinosyl ring. Likewise, when q is 0 and $R_2'$ is in the down configuration, the ring is an erythrosyl ring. When $R_2'$ and $R_4'$ are joined to form a bridge, the ring is called a locked nucleic acid (LNA), as described in greater detail herein. In some embodiments, the bridge formed by $R_2'$ and $R_4'$ is $R_2'$—O—$(CH_2)_r$—$R_4'$ (wherein r is 1 or 2) or $R_2'$—$CH_2$—O—$CH_2$—$R_4'$ (the use of $R_2'$ and $R_4'$ in the sub-formulae indicating the points of attachment). LNA may be present in either α-L- or β-D-conformation. Each of these analogs possesses a number of useful characteristics, including resistance to exonuclease activity, induction if endonuclease activity and modulation of hybridization.

When $R_4'$ and $R_5'$ form a bridge, they may form, along with the sugar ring to which they are attached, a tricyclic ring. Tricyclic nucleosides of the structure are as follows.

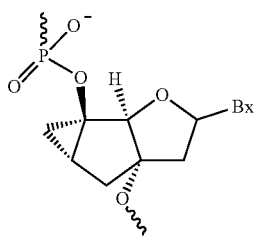

One skilled in the art will recognize that the analogous phosphorothioates, and 2'-substituted tricyclic deoxynucleosides may be prepared by substituting a sulfurizing oxidant for the oxidizing agent. The 2'-substituted tricyclic deoxynucleosides may be prepared from the analogous 2'-OH protecting group in the case of ribonucleic acid.

Suitable 2'-substituents corresponding to $R_2'$ include: F, O-alkyl (e.g. O-methyl), S-alkyl, N-alkyl, O-alkenyl, S-alkenyl, N-alkenyl, O-alkynyl, S-alkynyl, N-alkynyl, O-alkyl-O-alkyl, wherein the alkyl, alkenyl and alkynyl may be substituted or unsubstituted $C_1$ to $C_{10}$ alkyl or $C_2$ to $C_{10}$ alkenyl or alkynyl, respectively. Particularly preferred are $O[CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[CH_2)_gCH_3]_2$, where g and h are from 1 to about 10. Other preferred oligonucleotides comprise one of the following at the 2'-position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SO_2CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamics properties of an oligonucleotide, and other substituents having similar properties. A preferred 2'-modification is 2'-deoxy-2'-methoxyethoxy (2'-$OCH_2CH_2OCH_3$, also known as 2'-O-(2-methoxyethyl) or 2'-MOE ribosyl). Other preferred modifications include 2'-dimethy-laminooxyethoxy, i.e., a $O(CH_2)_2ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3)_2$.

Other preferred modifications include 2'-methoxy (2'-O—$CH_3$), 2'-aminopropoxy (2'—$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide.

Further representative substituent groups include groups of formula ($I_a$) or ($II_a$):

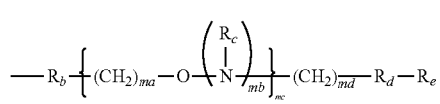
(Ia)

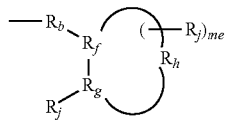
(IIa)

wherein:
$R_b$ is O, S or NH;
$R_d$ is a single bond, O or C(=O);
$R_e$ is $C_1$-$C_{10}$ alkyl, N($R_k$)($R_m$), N=C($R_p$)($R_q$), N=C($R_p$)($R_r$) or has formula (IIIa);

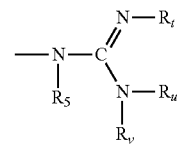

each $R_c$, $R_q$, $R_r$, $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$ together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

$R_k$ is hydrogen, a nitrogen protecting group or —$R_x$—$R_y$;
$R_p$ is hydrogen, a nitrogen protecting group or —$R_x$—$R_y$;
$R_x$ is a bond or a linking moiety;
$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH^{3+}$, N($R_u$)($R_v$), guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_i$ is $OR_z$, $SR_z$, or N($R_z$)$_2$; each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N($R_k$)($R_m$)$OR_k$, halo, $SR_k$ or CN;

ma is 1 to about 10;
mb is, independently, 0 or 1;
mc is 0 or an integer from 1 to 10;
md is an integer from 1 to 10;
me is from 0, 1 or 2; and
provided that when mc is 0, and is greater than 1.

Particularly preferred sugar substituent groups include $O[(CH_2)_gO]_hCH_3$, $O(CH_2)_gOCH_3$, $O(CH_2)_gNH_2$, $O(CH_2)_gCH_3$, $O(CH_2)_gONH_2$, and $O(CH_2)_gON[(CH_2)_gCH_3]_2$, where g and h are from 1 to about 10.

Some preferred oligomeric compounds of the disclosure contain at least one nucleoside having one of the following substituent groups: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligomeric compound, or a group for improving the pharmacodynamic properties of an oligomeric compound, and other substituents having similar properties. A preferred modification includes 2'-methoxyethoxy [2'-O—$CH_2CH_2OCH_3$, also known as 2'-O-(2-methoxyethyl) or 2'-MOE, i.e., an alkoxy-alkoxy group. A further preferred modification is 2'-dimethylaminooxyethoxy, i.e., a $O(CH_2)_2ON(CH_3)_2$ group, also known as 2'-DMAOE.

Nucleobases

The nucleobases Bx (also referred to in the art as nucleic acid bases or simply as bases) may be naturally-occurring G, C, A, U or T, or may be selected from a wide range of non-naturally occurring bases as described herein. The two most common classes of nucleobases are purines and pyrimidines. The naturally-occurring purine bases are guanine (G) and adenine (A), which are linked to the sugar through the 9-N nitrogen in the 13-anomeric position on the sugar ring. The naturally-occurring pyrimidine bases are uracil (U), thymine (T) and cytidine (C), which are linked to the sugar through the 1-N nitrogen. In double stranded DNA (dsDNA), Watson-Crick base pairing occurs between G and C, and between A and T. whereas in double stranded RNA (dsRNA), Watson-Crick base pairing occurs between G and C, and between A and U. The Watson-Crick base pairs for DNA and RNA are shown below.

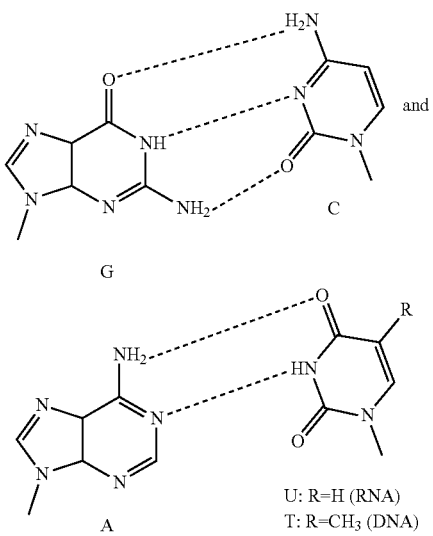

Analogous base pairing is generally observed in RNA-DNA hybrids, as well as in hybrids between naturally-occurring RNA or DNA and synthetic oligonucleotides comprising non-naturally occurring monomeric subunits.

In synthetic oligonucleotides according to the disclosure, one or more of the naturally-occurring nucleobases may be replaced by an analogous binding member (nucleobase analog). Thus, the term "nucleobase" encompasses both naturally-occurring and non-naturally-occurring nucleobases. The term "nucleobase analog" (also referred to herein is a nucleobase mimetic or a nucleic acid base mimetic) refers to non-naturally-occurring nucleobases, and means a residue that functions like a nucleobase by providing sequence specific binding to a heterocyclic residue on a complementary oligomer. In some embodiments according to the disclosure, a nucleobase analog is a residue that is capable of establishing one or more non-covalent bonds with a nucleobase on a separate oligonucleotide strand. Non-covalent bonds are hydrogen bonds, ionic bonds and polar interactions. (Additional interactions with non-complementary nucleobases are also possible, such as base-stacking interactions). In some embodiments of the disclosure, non-covalent bonds are formed by hydrogen bonding between nucleobase ring constituents and/or exocyclic substituents, and may be analogous to Watson-Crick bonding, Hoogsteen bonding, some combination thereof, or some other regime as described herein or as known in the art.

As used herein, "unmodified" or "natural" nucleobases mean the purine bases adenine (A) and guanine (G), and the pyrimidine bases thymine (T), cytosine (C) and uracil (U). Modified nucleobases (nucleobase analogs) include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine, 7-propynyl-7-deaza-8-azaguanine, 7-propynyl-7-deaza-8-azaadenine. Further modified nucleobases include tricyclic pyrimidines such as phenoxazine cytidine(1H-pyrimido[5,4b][1,4]benzoxazin-2(3H)-one), phenothiazine cytidine (1H-pyrimido[5,4-b][1,4]benzothiazin-2(3H)one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5][pyrrolo][2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone.

Certain of these nucleobases are particularly useful for increasing the binding affinity of the oligomeric compounds of the disclosure. These include 5-substituted pyrimidines, 6-azapyrimidines and N-2, N-6 and O-6 substituted purines, including 2-aminopropyladenine, 5-propynyluracil and 5-propynylcytosine.

In general, the term "base" includes the term nucleobase as described above. The term "base" means a binding member, as described hereinabove. While nucleobases are generally heterocyclic moieties, the term "base" as used herein with means any moiety or residue capable of participating in specific binding to a naturally-occurring nucleobase.

In some embodiments of the present disclosure oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand.

In the context of this disclosure, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary" as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

Phosphate Linkers

Oligonucleotides are generally those oligomers in which the monomeric subunits comprise linking members having pentavalent phosphorus as a constituent part. Phosphate linkers include phosphodiester, phosphorothioate and phosphorodithioate linkers.

Naturally occurring nucleosides are linked to one another via a phosphodiester linker. Antisense compounds may be prepared using phosphodiester linkers, which are generally suitable for diagnostic and other nuclease-free uses. However, antisense therapeutic compounds advantageously comprise at least one phosphorothioate linker, owing to the latter's superior nuclease stability. Both phosphodiester and phosphorothioate diester linkers are generally referred to as phosphate diester linkers. When a plurality of nucleotides are linked by successive phosphate diester linkers, the resulting oligomer is called an oligonucleotide.

Oligonucleotides Synthesis

As described above, the term "oligonucleotide" encompasses naturally-occurring RNA and DNA as well as phosphate-linked oligomers having a variety of sugar backbones and nucleobases. Oligonucleotides have been made by the phosphate triester, H-phosphonate and phosphoramidite methods as described hereinabove. Of these three methods, the phosphoramidite method has become the de facto standard for oligonucleotide synthesis, especially where one or more modifications are made to the sugar backbone or nucleobases, or where exceptional purity, yield or scale are paramount. The phosphoramidite method (amidite method) is described hereinafter.

Amidite Method

While the present disclosure is concerned primarily with oligonucleotides, some oligonucleotide mimetics may, with appropriate changes to the starting materials, also be prepared by processes according to the present disclosure. Oligonucleotide mimetics include compounds in which the oligonucleotide sugar has been replaced with a heterocyclic or carbocyclic ring structure. Such compounds are depicted in Formula (I-1), below,

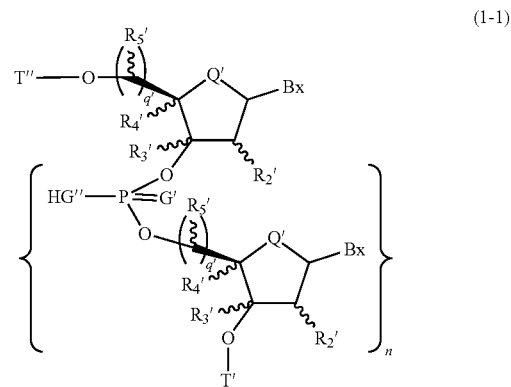

(1-1)

and tautomers, salts and solvates thereof, wherein G', G", Bx, n, $R_2'$, $R_3'$, $R_4'$, and $R_5'$, each have the meanings previously defined. The groups T' and T" are each H, or conjugate groups, such as protecting groups and substituents. Each Q' is independently O, S, NR''', C(R''')$_2$, or —CR'''=CR'''—, where each R''' is H, alkyl, or where two R''' groups are on the same or adjacent carbon atoms, they may form a carbocyclic or heterocyclic ring, wherein the ring contains one or two of N, O or S. Preferred values of R''' are H and $C_1$-$C_4$ alkyl.

The foregoing oligonucleotides and oligonucleotide mimetics may be synthesized by solid phase synthesis, e.g. by the amidite method. Other means for such synthesis known in the art may additionally or alternatively be employed.

Support bound oligonucleotide synthesis relies on sequential addition of nucleotides to one end of a growing chain. Typically, a first nucleoside (having protecting groups on any exocyclic amine functionalities present) is attached to an appropriate glass bead support and activated phosphite compounds (typically nucleotide phosphoramidites, also bearing appropriate protecting groups) are added stepwise to elongate the growing oligonucleotide.

The amidite method of oligonucleotide synthesis may be carried out generally in the following manner reacting a suitable nucleoside or modified nucleoside (formula (4)) with a phosphorodiamidite (formula (5)) to form a phosphramidite (formula (6)):

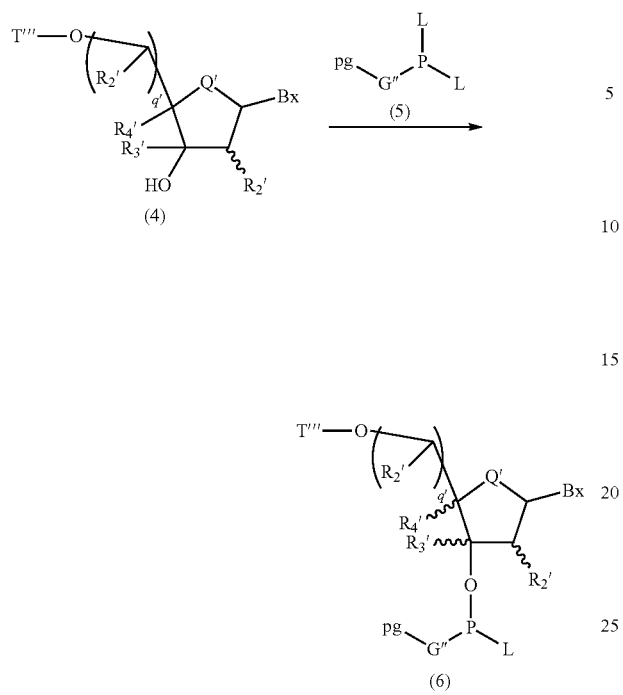

(4)

(5)

(6)

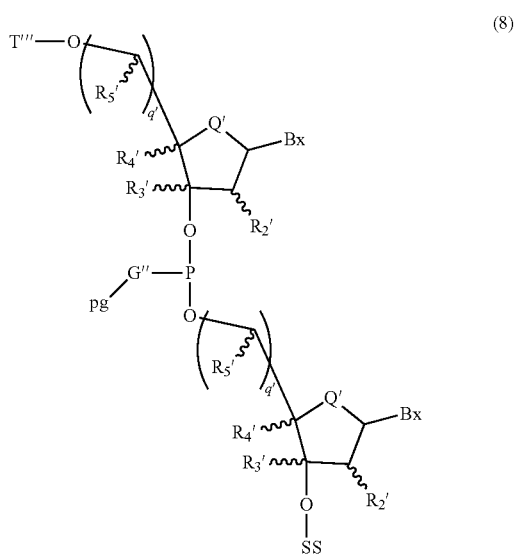

(8)

wherein each of the variables Q', Bx, $R_2'$, $R_3'$, $R_4'$, $R_5'$, G" and q' is as previously defined. L is an amine leaving group; pg is a phosphors protecting group; and T'" is a hydroxyl protecting group, each as more specifically defined herein. In some embodiments of the present disclosure, in at least one cycle of the synthetic method, T'" is DMT.

A support-bond nucleoside of Formula (7) is first deprotected at the 5'-position (resulting in a free 5'-OH group). In some embodiments of the present disclosure, at least one of the 5-protecting groups (T'") is DMT, and the deprotecting reagent is the composition or the DCA reagent as defined above. In more specific embodiments of the present disclosure, a plurality of 5'-deprotection steps are carried out in the presence of the composition or the DCA reagent as defined above. In certain embodiments of the present disclosure, each of the 5'-deprotection steps is carried out in the presence of the composition or the DCA reagent as defined above, optionally in a suitable solvent, such as acetonitrile or toluene.

After 5'-deprotection, a first amidite (7) is coupled to a support-bond nucleoside to form a support-bond dimer of Formula (8), which is then oxidized, and subjected to a capping step to form a support bond dimer of Formula (9).

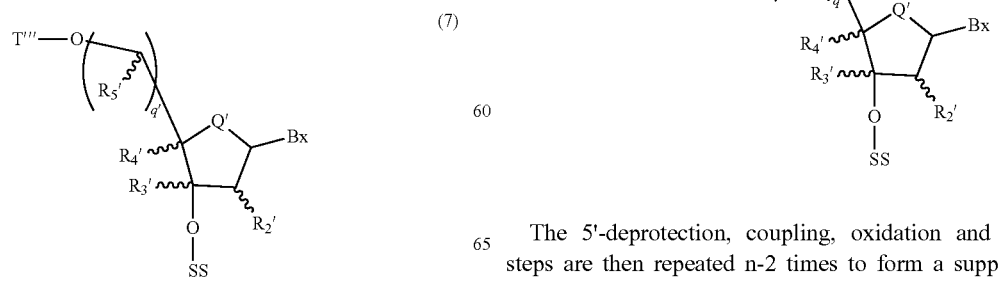

(7)

(9)

The 5'-deprotection, coupling, oxidation and capping steps are then repeated n-2 times to form a support-bond oligomer of Formula (10).

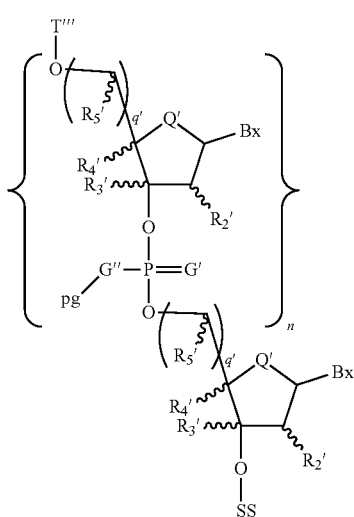

(10)

This compound (10) is then cleaved from the solid support, 5'-deprotected, if necessary, and purified to yield an oligomer of Formula (I). The oligonucleotide may then be further derivatized, purified, precipitated, or otherwise treated, as described in more detail herein. In select embodiments of the present invention, the final protecting group is left on the oligonucleotide (10, SS replaced by H), which is first subjected to high performance liquid chromatography (HPLC), before the final 5'-protecting group is removed. In specific embodiments of the present invention, the final 5'-protecting group is removed by contacting the purified oligonucleotide with acetic acid. In other embodiments the 5'-protecting group may be removed while the oligonucleotide is left on the solid support (SS). The deprotected oligonucleotide (10, wherein T'''; is replaced by H) may then be removed from the column as described above and subjected to purification steps. In specific embodiments of the invention, a deprotected oligonucleotide may be subjected to ion exchange chromatography, such as soft anion exchange (SAX) chromatography. Anion exchange chromatography may be carried out either directly after a deprotected oligonucleotide is removed from the solid synthesis support, or after a 5'-protected oligonucleotide has been purified by liquid chromatography and then deprotected.

In each of the foregoing Formulae, SS represents a support bound to the 3'-terminal nucleoside by a cleavable linker, each pg is a phosphorus protecting group as defined herein, n is an integer, G' and G'' are independently O or S, and each Bx, $R_2'$, $R_3'$, $R_4'$, $R_5'$, Q', and q' is independently as defined above.

Amidites

Phosphoramidites (amidites) used in the synthesis of oligonucleotides are available from a variety of commercial sources. Commercially available phosphoramidites are prepared for the most part for automated DNA synthesis and as such are prepared for immediate use for synthesizing desired sequences of oligonucleotides.

Support Media

Oligonucleotides are generally prepared, as described above, on a support medium (support), e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support media can be soluble or insoluble, or may possess variable solubility in different solvents to allow the growing support bound polymer to be either in or out of solution as desired. Traditional support media such as solid supports are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis.

The term support media (support) is intended to include supports known to the person skilled in the art to for the synthesis of oligomeric compounds and related compounds such as peptides. Some representative support media that are amenable to the methods of the present disclosure include but are not limited to the following: controlled pore glass (CPG); oxalyl-controlled pore glass; silica-containing particles, such as porous glass beads and silica gel such as that formed by the reaction of trichloro-[3-(4-chloromethyl)phenyl]propylsilane and porous glass beads; the mono ester of 1,4-dihydroxymethylbenzene and silica; TENTAGEL; cross-linked styrene/divinylbenzene copolymer beaded matrix or POROS, a copolymer of polystyrene/divinylbenzene; soluble support media, polyethylene glycol PEG's.

In a certain embodiment, the support media is, for example, polystyrene primer dT 350 support.

Equipment for Synthesis

Commercially available equipment routinely used for the support media based synthesis of oligomeric compounds and related compounds. In certain embodiments, the equipment used for the support media is, for example, automated AKTA OP100 Synthesizer with 6.3 mL reaction column. Any other means for such synthesis known in the art may additionally or alternatively be employed.

Phosphorus Protecting Groups

In general, the phosphorus protecting group (pg) is an alkyl group or a β-eliminable group having the formula —$CH_2CH_2$-$G_w$, wherein $G_w$ is an electron-withdrawing group. In general the alkyl or cyanoethyl withdrawing groups are preferred, as commercially available phosphoramidites generally incorporate either the methyl or cyanoethyl phosphorus protecting group.

The method for removal of phosphorus protecting groups (pg's) depends upon the specific pg to be removed. The β-eliminable groups are generally removed in a weak base solution, whereby an acidic β-hydrogen is extracted and the —$CH_2CH_2$-$G_w$ group is eliminated by rearrangement to form the corresponding acrylo-compound $CH_2$=CH-$G_w$. In contrast, an alkyl group is generally removed by nucleophilic attack on the α-carbon of the alkyl group.

Coupling

Before coupling, the amidite needs to be activated. In certain embodiments, the amidite is activated with tetrazole, 5-(ethylthio)-1H-tetrazole (ETT) or 5-(benzylthio)-1H-tetrazole (BTT). Various solvents, acetonitrile, etc., may be used in the coupling. In some embodiments, the coupling recycle consists of co-delivery of 2.0 equivalents of 0.2M amidite solution in acetonitrile and 0.6 M ETT in acetonitrile in a 2:3 flow ratio over the course of 0.5 min, recirculation through the column for 4 min.

Oxidation (Including Sulfurization)

The person skilled in the art will recognize that oxidation of P(III) to P(V) can be carried out by a variety of reagents. Furthermore, the person skilled in the art will recognize that the P(V) species can exist as phosphate triesters, phosphorothioate diesters, or phosphorodithioate diesters. Each type of P(V) linkage has uses and advantages, as described herein. Thus, the term "oxidizing agent" should be understood broadly as being any reagent capable of transforming a P(III) species (e.g. a phosphite) into a P(V) species. Thus the term "oxidizing agent" includes "sulfurizing agent" and oxidation will be understood to embrace both introduction of oxygen and introduction of sulfur, or sulfurization. Where it is important to indicate that an oxidizing agent introduces an oxygen into a P(III) species to make a P(V) species, the oxidizing agent will be referred to herein is "an oxygen-introducing oxidizing reagent".

Oxidizing reagents for making phosphate diester linkages under the phosphoramidite protocol are known in the art, such as iodine. Examples of sulfurization reagents which have been used to synthesize oligonucleotides containing phosphorothioate bonds include elemental sulfur, dibenzoyltetrasulfide, 3-H-1,2-benzidithiol-3-one-1,1-dioxide (also known as Beaucage reagent), tetraethylthiuram disulfide (TETD), and bis-(O,O-diisopropoxy phosphinothioyl) disulfide (known as Stec reagent). Oxidizing reagents for making phosphorothioate diester linkages include phenyl acetyl disulfide (PADS). In some embodiments of the disclosure, the phosphorothioate diester and phosphate diester linkages may alternate between sugar subunits. In other embodiments of the present disclosure, phosphorothioate linkages alone may be employed.

Various solvents, acetonitrile, toluene, xanthenes, dichloromethane, pyridine, water, etc., may be used in the oxidation reaction. In certain embodiments, the solvent in the oxidation reaction is a mixture of pyridine and water (for example pyridine:water=9:1, v/v).

Cleavage and Workup

Reagents for cleaving an oligonucleotide from a support are common reagents in the art.

The oligonucleotide may be worked up by standard procedures known in the art, for example by size exclusion chromatography, high performance liquid chromatography (e g. reverse-phase HPLC), differential precipitation, etc. In some embodiments according to the present disclosure, the oligonucleotide is cleaved from a solid support while the 5'-OH protecting group is still on the ultimate nucleoside. This so-called DMT-on (or trityl-on) oligonucleotide is then subjected to chromatography, after which the DMT group is removed by treatment in an organic acid, after which the oligonucleotide is de-salted and further purified to form a final product.

Removal of 5-protection after cleavage of the oligonucleotide from the support is generally performed with acetic acid.

As used herein "oligonucleotide synthesis" is intend to have its art-recognized meaning whereby an oligonucleotide is prepared using synthetic methods well known to the ordinarily skilled artisan. See for example: U.S. Pat. Nos. 7,169,916, 6,069,243 and 6,399,765, each of which are hereby incorporated by reference in their entirety.

In a sixth aspect, the present disclosure provides a method for detecting glyoxylic acid in a sample of DCA.

The sample of DCA of the present disclosure may be selected from the composition or the DCA reagent as defined above or commercially available DCA products.

In certain embodiments, the method for detecting glyoxylic acid is IC method.

In the IC method, the standard substance is glyoxylic acid, such as glyoxylic acid monohydrate, which is commercially available (e.g. Aladin; Lot #F1714025).

In the IC method, preferably, the qualitative analysis is based on retention time.

In the IC method, preferably, the content of the glyoxylic acid in the sample of DCA is quantified by using external standard method.

In the external standard method, the content of the glyoxylic acid in the sample of DCA is calculated based on the content of STD solution using conventional method in the art.

The mobile phase in the IC method is, for example, 20 mM KOH aqueous solution.

The column in the IC method is, for example, Dionex IonPac AS18.

The specification of the column in the IC method is, for example, 4 mm×250 mm.

The flow rate of the column in the IC method is, for example, 1.0 mL/min.

The injection volume of the column in the IC method is, for example, 25 μL.

The analysis time of the column in the IC method is, for example, 20 min.

The conditions of the IC method are as follows:
Instrument: ICS-6000;
Column Dionex IonPac AS18, 4 mm×250 mm;
Mobile phase: KOH (RFC):20 mM aqueous solution (RFC: Reagent free controller);
Flow rate: 1.0 mL/min;
Aers-4 mm Suppressor: 50 mA;
Injection volume: 25 μL; and
Analysis time: 20 min.

In a seventh aspect, the present disclosure provides methods for measuring the concentration of glyoxylic acid in the composition or the DCA reagent as defined above or commercially available DCA products, particularly, for detecting glyoxylic acid and measuring its concentration in the composition or the DCA reagent as defined above or commercially available DCA products. In certain embodiments, the methods are IC method as defined above.

In certain embodiments, the present disclosure provides an analytical method comprising determining whether or not an ion chromatography spectrum taken from a sample of DCA includes a chromatographic peak associated with glyoxylic acid.

The existing DCA products (such as commercially available DCA products) are prepared by different processes, which makes DCA almost impossible to be a pure chemical substance (i.e., 100% dichloroacetic acid). Therefore, the dichloroacetic acid products contain more or less impurities. Therefore, in certain embodiments, each of the composition and the DCA reagent of the present disclosure further comprises an impurity or some impurities (excluding glyoxylic acid), which may not have effect on oligonucleotide synthesis.

In certain embodiments, in the composition or the DCA reagent, the total content of the other impurities is, for example, below 0.2%, such as below 0.9%, 0.8%. 0.7%, 0.6%, 0.5%, 0.4%, 0.3%, 0.2%, 0.1%, 0.09%, 0.08%, 0.07%, 0.06%, 0.05%, 0.04%, 0.03%, 0.02% and 0.01%. In certain embodiments, in the composition or the DCA reagent, the content of one single impurity (other impurities) is determined by, for example, IC method. The IC method is as defined in the disclosure. Preferably, the content of one single impurity (other impurities) is quantified by the area normalization method.

In certain embodiments, the composition of the present disclosure comprises, consists essentially of, or consists of DCA and one or more impurities that have no adverse effect on oligonucleotide synthesis. In certain embodiments, the composition of the present disclosure comprises, consists essentially of, or consists of DCA, glyoxylic acid and other impurities. In some embodiments, an impurity may be regarded as having no adverse effect on oligonucleotide synthesis when removing or reducing the level of the impurity does not increase the yield and/or purity of a target oligonucleotide (e.g., in a model synthesis of Oligodeoxyribonucleotide T10). In some embodiments, an impurity may be regarded as having no adverse effect on oligonucleotide synthesis when the level of the impurity in a DCA composition is sufficiently low such that it does not cause a decrease of the yield and/or purity of a target oligonucleotide (e.g., in a model synthesis of Oligodeoxyribonucleotide T10) when compared with that using a DCA composition without the impurity in the oligonucleotide synthesis. The content of DCA and glyoxylic in the composition include those defined above.

Each of the composition and the DCA reagent of the present disclosure does not comprise known impurities in the art (such as chloral hydrate) in DCA products reported in the prior art that will have effect on oligonucleotide synthesis. If such impurities are present, the amount of which is an amount that has no effect on oligonucleotide synthesis.

In an eighth aspect, the present disclosure provides a method of synthesizing an oligonucleotide, comprising:

a) selecting or identifying a substantially pure dichloroacetic acid that comprises less than 1,000 ppm glyoxylic acid (e.g., described herein, such as less than 50 ppm, preferably less than 15 ppm, more preferably, less than 2.5 ppm, such as non-detectable); and b) mixing the substantially pure dichloroacetic acid with a protected oligonucleotide having an acid labile protecting group under conditions suitable to remove the acid labile protecting group, thereby producing a deprotected oligonucleotide. As used herein, "non-detectable" should be understood as below the limit of detection or below the limit of quantification of a suitable analytical method described herein, such as an ionic chromatography method described herein.

In some embodiments of the present disclosure, in the method described above, the selecting or identifying comprises a step of determining or having determined whether a test substantially pure dichloroacetic acid comprises less than 1,000 ppm glyoxylic acid (e.g., described herein, such as less than 50 ppm, preferably less than 15 ppm, more preferably, less than 2.5 ppm, such as non-detectable).

In some embodiments of the present disclosure, in the method described above, the selecting or identifying comprises a step of determining or having determined whether a test substantially pure dichloroacetic acid comprises less than 1,000 ppm glyoxylic acid (e.g., described herein, such as less than 50 ppm, preferably less than 15 ppm, more preferably, less than 2.5 ppm, such as non-detectable) by ion chromatography (e.g., described herein).

In some embodiments of the present disclosure, in the method described above, the protected oligonucleotide comprises a 5'-hydroxyl protected with the acid labile protecting group. As those skilled in the art would understand, the methods herein are not particularly limited to preparing any specific oligonucleotide, any of those oligonucleotides known in the art using an acid labile protecting group (such as a trityl group, e.g., DMT) during the synthesis can be prepared by the methods herein. The methods herein are also not particularly limited to any specific protected oligonucleotide. Any of those know in the art with an acid labile protecting group that can be deprotected with DCA can be used in the methods herein.

In some embodiments of the present disclosure, in the method described above, the acid labile protecting group is a trityl group, preferably, a 4,4'-dimethoxytriphenylmethyl. Other suitable acid labile protecting groups include those known in the art.

In some embodiments of the present disclosure, in the method described above, the protected oligonucleotide is bound to a solid support (e.g., any of those known in the art as suitable).

In some embodiments of the present disclosure, in the method described above, the mixing comprises mixing the substantially pure dichloroacetic acid with the protected oligonucleotide in a solvent, such as toluene. To be clear, in such embodiments, the substantially pure dichloroacetic acid is typically mixed with the solvent first, for example, as a solution containing 5%, 10%, 20%, 30% 40%, 50%, 80%, 90%, or any range between the recited values, by weight, and the solution can then be mixed with the protected oligonucleotide. Further, more than one solvents can be used. For example, in some embodiments, the protected oligonucleotide can be in contact with a second solvent (which can be the same as or different from the solvent), before the solution of the substantially pure dichloroacetic acid is added to mix with the protected oligonucleotide, along with the second solvent. Other expressions regarding mixing in a solvent as described herein should be understood similarly.

In some embodiments of the present disclosure, the method described above further comprises converting the deprotected oligonucleotide into an oligonucleotide with a desired sequence.

In a ninth aspect, the present disclosure provides a method of synthesizing an oligonucleotide, comprising:

a) preparing or having prepared a substantially pure dichloroacetic acid having less than 1000 ppm glyoxylic acid (e.g., described herein, such as less than 50 ppm, preferably less than 15 ppm, more preferably, less than 2.5 ppm, such as non-detectable); and b) mixing the substantially pure dichloroacetic acid with a protected oligonucleotide having an acid labile protecting group under conditions suitable to remove the acid labile protecting group, thereby producing a deprotected oligonucleotide. Conditions suitable for removing acid labile protecting groups by DCA are generally known in the art and are also exemplified in the present disclosure.

In some embodiments of the present disclosure, in the method described above, prior to the mixing, the substantially pure dichloroacetic acid is determined to comprise less than 1,000 ppm glyoxylic acid (e.g., described herein, such as less than 50 ppm, preferably less than 15 ppm, more preferably, less than 2.5 ppm, such as non-detectable).

In some embodiments of the present disclosure, in the method described above, prior to the mixing, the substantially pure dichloroacetic acid is determined to comprise less than 1,000 ppm glyoxylic acid (e.g., described herein, such as less than 50 ppm, preferably less than 15 ppm, more preferably, less than 2.5 ppm, such as non-detectable) by ion chromatography.

In some embodiments of the present disclosure, in the method described above, the substantially pure dichloroacetic acid is prepared from a starting dichloroacetic acid composition having glyoxylic acid by reducing the level of glyoxylic acid to less than 1,000 ppm (e.g., described herein, such as less than 50 ppm, preferably less than 15 ppm, more preferably, less than 2.5 ppm, such as non-detectable).

In some embodiments of the present disclosure, in the method described above, the substantially pure dichloroacetic acid is prepared from reacting the starting dichloroacetic acid composition with a glyoxylic acid capture reagent to reduce the level of glyoxylic acid to less than 1,000 ppm (e.g., described herein, such as less than 50 ppm, preferably less than 15 ppm, more preferably, less than 2.5 ppm, such as non-detectable).

In some embodiments of the present disclosure, in the method described above, the protected oligonucleotide comprises a 5'-hydroxyl protected with the acid labile protecting group.

In some embodiments of the present disclosure, in the method described above, the acid labile protecting group is a trityl group, preferably, a 4,4'-dimethoxytriphenylmethyl.

In some embodiments of the present disclosure, in the method described above, the protected oligonucleotide is bound to a solid support.

In some embodiments of the present disclosure, in the method described above, the mixing comprises mixing the substantially pure dichloroacetic acid with the protected oligonucleotide in a solvent, such as toluene.

In some embodiments of the present disclosure, the method described above further comprising converting the deprotected oligonucleotide into an oligonucleotide with a desired sequence.

In a tenth aspect, the present disclosure provides a method of synthesizing an oligonucleotide, the method comprising:
a) determining or having determined a substantially pure dichloroacetic acid as having less than 1,000 ppm glyoxylic acid (e.g., described herein, such as less than 50 ppm, preferably less than 15 ppm, more preferably, less than 2.5 ppm, such as non-detectable); and
b) mixing the substantially pure dichloroacetic acid with a protected oligonucleotide having an acid labile protecting group under conditions suitable to remove the acid labile protecting group, thereby producing a deprotected oligonucleotide.

In some embodiments of the present disclosure, the method described above comprising determining or having determined the substantially pure dichloroacetic acid as having less than 1,000 ppm glyoxylic acid (e.g., described herein, such as less than 50 ppm, preferably less than 15 ppm, more preferably, less than 2.5 ppm, such as non-detectable) by ion chromatography.

In some embodiments of the present disclosure, in the method described above, the protected oligonucleotide comprises a 5'-hydroxyl protected with the acid labile protecting group.

In some embodiments of the present disclosure, in the method described above, the acid labile protecting group is a trityl group, preferably, a 4,4'-dimethoxytriphenylmethyl.

In some embodiments of the present disclosure, in the method described above, the protected oligonucleotide is bound to a solid support.

In some embodiments of the present disclosure, in the method described above, the mixing comprises mixing the substantially pure dichloroacetic acid with the protected oligonucleotide in a solvent, such as toluene.

In some embodiments of the present disclosure, the method described above further comprising converting the deprotected oligonucleotide into an oligonucleotide with a desired sequence.

In an eleventh aspect, the present disclosure provides a method of synthesizing an oligonucleotide, the method comprising:
a) mixing a substantially pure dichloroacetic acid with a protected oligonucleotide of a first sequence having an acid labile protecting group under conditions suitable to remove the acid labile protecting group, thereby providing an oligonucleotide of the first sequence;
b) reacting the oligonucleotide of the first sequence with a desired nucleotide protected with a second protecting group under conditions to elongate the nucleotide chain to form a protected oligonucleotide of a second sequence with the second protecting group;
c) deprotecting the protected oligonucleotide of the second sequence to remove the second protecting group; and optionally
d) repeating the steps of b) and c) until a desired sequence is reached,
wherein the substantially pure dichloroacetic acid is determined to have less than 1000 ppm glyoxylic acid (e.g., described herein, such as less than 50 ppm, preferably less than 15 ppm, more preferably, less than 2.5 ppm, such as non-detectable).

In a twelfth aspect, the present disclosure provides a method of removing an acid labile protecting group from a protected oligonucleotide, the method comprising:
a) determining or having determined a substantially pure dichloroacetic acid as having less than 1,000 ppm glyoxylic acid (e.g., described herein, such as less than 50 ppm, preferably less than 15 ppm, more preferably, less than 2.5 ppm, such as non-detectable); and
b) mixing the substantially pure dichloroacetic acid with the protected oligonucleotide under conditions suitable to remove the acid labile protecting group.

In some embodiments of the present disclosure, the method described above comprises determining or having determined the substantially pure dichloroacetic acid as having less than 1,000 ppm glyoxylic acid (e.g., described herein, such as less than 50 ppm, preferably less than 15 ppm, more preferably, less than 2.5 ppm, such as non-detectable) by ion chromatography.

In some embodiments of the present disclosure, in the method described above, the protected oligonucleotide comprises a 5'-hydroxyl protected with the acid labile protecting group.

In some embodiments of the present disclosure, in the method described above, the acid labile protecting group is a trityl group, preferably, a 4,4'-dimethoxytriphenylmethyl.

In some embodiments of the present disclosure, in the method described above, the protected oligonucleotide is bound to a solid support.

In some embodiments of the present disclosure, in the method described above, the mixing comprises mixing the substantially pure dichloroacetic acid with the protected oligonucleotide in a solvent, such as toluene.

In a thirteenth aspect, the present disclosure provides a method of selecting or identifying a substantially pure dichloroacetic acid for oligonucleotide synthesis, the method comprising 1) determining or having determined the level of glyoxylic acid in a test substantially pure dichloroacetic acid, for example, by ion chromatography; and optionally 2) selecting or identifying a substantially pure dichloroacetic acid having less than 1000 ppm glyoxylic acid (e.g., described herein, such as less than 50 ppm, preferably less than 15 ppm, more preferably, less than 2.5 ppm, such as non-detectable) for oligonucleotide synthesis.

In a fourteenth aspect, the present disclosure provides a method of analyzing a dichloroacetic acid composition, comprising determining the level of glyoxylic acid in the dichloroacetic acid composition, for example, by ion chromatography.

In a fifteenth aspect, the present disclosure provides a method of producing a dichloroacetic acid composition, comprising 1) analyzing the level of glyoxylic acid in a starting dichloroacetic acid composition, for example, by ion chromatography; and optionally 2) reducing the level of glyoxylic acid in the starting dichloroacetic acid composition to be less than 1000 ppm (e.g., described herein, such as less than 50 ppm, preferably less than 15 ppm, more preferably, less than 2.5 ppm, such as non-detectable), for example, by mixing the starting dichloroacetic acid composition with a glyoxylic acid capture agent (e.g., described herein), thereby producing the dichloroacetic acid composition.

The term "dichloroacetic acid (DCA)" refers to a chemical compound having the structure of $Cl_2CHC(=O)(OH)$.

The term "substantially pure dichloroacetic acid" refers to dichloroacetic acid having a purity of greater than 90% (e.g., greater than 95%, greater than 98%, greater than 99%, or greater than 99.5%), by weight, GC area, by IC method, or any combination thereof.

In any of the embodiments described herein, unless otherwise specified or obvious from context, the substantially pure dichloroacetic acid can comprise less than 950 ppm, 900 ppm, 800 ppm, 700 ppm, 600 ppm, 500 ppm, 400 ppm, 300 ppm, 200 ppm, 100 ppm, 50 ppm, 40 ppm, 30 ppm, 20 ppm, 10 ppm, 9 ppm, 8 ppm, 7 ppm, 6 ppm, 5 ppm, 4 ppm, 3.5 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.1 ppm, 1.05 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm glyoxylic acid (by weight, GC area, by IC method, or any combination thereof).

In any of the embodiments described herein, unless otherwise specified or obvious from context, the substantially pure dichloroacetic acid can comprise less than 500 ppm, 450 ppm, 400 ppm, 350 ppm, 300 ppm, 250 ppm, 200 ppm, 150 ppm, 100 ppm, 90 ppm, 80 ppm, 70 ppm, 60 ppm, 50 ppm, 40 ppm, 30 ppm, 20 ppm, 15 ppm, 12 ppm, 10 ppm, 9 ppm, 8 ppm, 7 ppm, 6 ppm, 5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm (by weight, GC area, by IC method, or any combination thereof).

In any of the embodiments described herein, unless otherwise specified or obvious from context, the substantially pure dichloroacetic acid can comprise less than 50 ppm, 45 ppm, 40 ppm, 35 ppm, 30 ppm, 25 ppm, 20 ppm, 15 ppm, 12 ppm, 10 ppm, 9 ppm, 8 ppm, 7 ppm, 6 ppm, 5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm or 0.05 ppm (by weight, GC area, by IC method, or any combination thereof).

In any of the embodiments described herein, unless otherwise specified or obvious from context, the substantially pure dichloroacetic acid can comprise less than 15 ppm, 14.5 ppm, 14 ppm, 13.5 ppm, 13 ppm, 12.5 ppm, 12 ppm, 11.5 ppm, 11 ppm, 10.5 ppm, 10 ppm, 9.5 ppm, 9 ppm, 8.5 ppm, 8 ppm, 7.5 ppm, 7 ppm, 6.5 ppm, 6 ppm, 5.5 ppm, 5 ppm, 4.5 ppm, 4 ppm, 3.5 ppm, 3.09 ppm, 3 ppm, 2.5 ppm, 2.45 ppm, 2.4 ppm, 2.35 ppm, 2.3 ppm, 2.25 ppm, 2.2 ppm, 2.15 ppm, 2.1 ppm, 2.05 ppm, 2 ppm, 1.95 ppm, 1.9 ppm, 1.85 ppm, 1.8 ppm, 1.75 ppm, 1.7 ppm, 1.65 ppm, 1.6 ppm, 1.55 ppm, 1.5 ppm, 1.45 ppm, 1.4 ppm, 1.35 ppm, 1.3 ppm, 1.25 ppm, 1.2 ppm, 1.15 ppm, 1.04 ppm, 1.1 ppm, 1.05 ppm, 1.01 ppm, 1 ppm, 0.95 ppm, 0.9 ppm, 0.85 ppm, 0.8 ppm, 0.75 ppm, 0.7 ppm, 0.65 ppm, 0.6 ppm, 0.55 ppm, 0.5 ppm, 0.45 ppm, 0.4 ppm, 0.35 ppm, 0.3 ppm, 0.25 ppm, 0.2 ppm, 0.15 ppm, 0.1 ppm or 0.05 ppm (by weight, GC area, by IC method, or any combination thereof).

In certain embodiments of the present disclosure, the substantially pure dichloroacetic acid is essentially free of glyoxylic acid, particularly, such as free of glyoxylic acid or having no detectable amount of glyoxylic acid (by weight, GC area, by IC method, or any combination thereof).

The term "glyoxylic acid" refers to a chemical compound having the structure of CHOCOOH.

The term "DCA reagent" refers to pure dichloroacetic acid, or has the same definitions as the composition as described in the present disclosure.

The term "a (the) sample of DCA (DCA sample)" refers to any DCA products, for example, the composition or the DCA reagent as described in the present disclosure, or DCA products prepared by any methods, or any commercially available DCA products.

In certain embodiments, each of the term "a (the) test substantially pure dichloroacetic acid", "a (the) starting dichloroacetic acid composition" may have the same definition as the term "a (the) sample of DCA (DCA sample)".

Abbreviations

DCA represents for dichloroacetic acid;
DMT represents for 4,4'-dimethoxytriphenylmethyl;
ETT represents for 5-(ethylthio)-1H-tetrazole;
CV represents for Column Volume;
$GA.H_2O$ represents for glyoxylic acid monohydrate;
GA represents for glyoxylic acid;
RFC represents for reagent free controller;
min represents for minute(s);
hr(s) represents for hour(s);
STD represents for standard substance.

EXAMPLES

The following examples further illustrate the present disclosure, but the present disclosure is not limited thereto.

Equipment $^1$-NMR: Bruker NMR.
$^{13}$-C NMR: Bruker NMR.
LC-MS: Waters Q-TOF, and Agilent LC-MS model: Agilent 1290+MSD.
HPLC: Agilent HPLC model: Agilent 1260.
Oligonucleotide Synthesizer: Automated AKTA OP100 Synthesizer (6.3 mL reaction column).
DCA sample-01 is purchased Changzhou Wujin Changxin Teaching Chemical Co., Ltd.
DCA sample-02 is purchased from Cabbe, Acros.
DCA reagents are prepared according to the methods of the present disclosure.

Example 1: Oligonucleotide Synthesis 1.1. Synthesis of Oligodeoxyribonucleotide T10

Oligodeoxyribonucleotide T10 was synthesized using standard phosphoramidite chemistry at 0.2 mmol scale on polystyrene primer dT 350 support using an automated AKTA OP100 Synthesizer with 6.3 mL reaction column.

For each amidite assembly, four chemical reactions were conducted including detritylation (5'-deprotection), coupling, oxidization and capping.

The detritlyation was conducted using 10% DCA sample-02 in toluene (v/v) with UV 350 nm monitoring control. The coupling recycle consists of co-delivery of 2.0 equivalents of 0.2M amidite solution in acetonitrile and 0.6 M ETT in acetonitrile in a 2:3 flow ratio over the course of 0.5 min, recirculation through the column for 4 min, oxidation with 0.05 M iodine in 9:1 pyridine:water (v/v), capping with 0.5 CV (column volume) of a capping mixture (1:1, v/v) of acetic anhydride acetonitrile (1:4, v/v) and N-methylimidazole-pyridine-acetonitrile (2:3:5, v/v/v) in 0.5 min), and washing with acetonitrile at each block. After 10 rounds of solid phase assembly, 10mer of oligonucleotide modified solid support was obtained.

1.2. Synthesis of Oligodeoxyribonucleotide T11

Then the detritylation time using 10% DCA sample-01 in toluene was increased when assembling the 11th dT amidite on to the solid support. After increasing detritylation time to 90 min, the coupling wasn't run again, which indicated some moieties captured the 5'-OH on the solid support.

After cleaving the oligonucleotide from support and checking by LC-MS, the main product was 10mer dT product, which indicated that the synthesis of oligodeoxyribonucleotide T11 failed.

SS~T
⟶
( )
9 cycles
SS~T~T~T~T~T~T~T~T~T ⟶
SS~T~T~T~T~T~T~T~T~T~T
↓
T~T~T~T~T~T~T~T~T~T

Example 2: Analysis of DCA Sample-01

Figure 1:
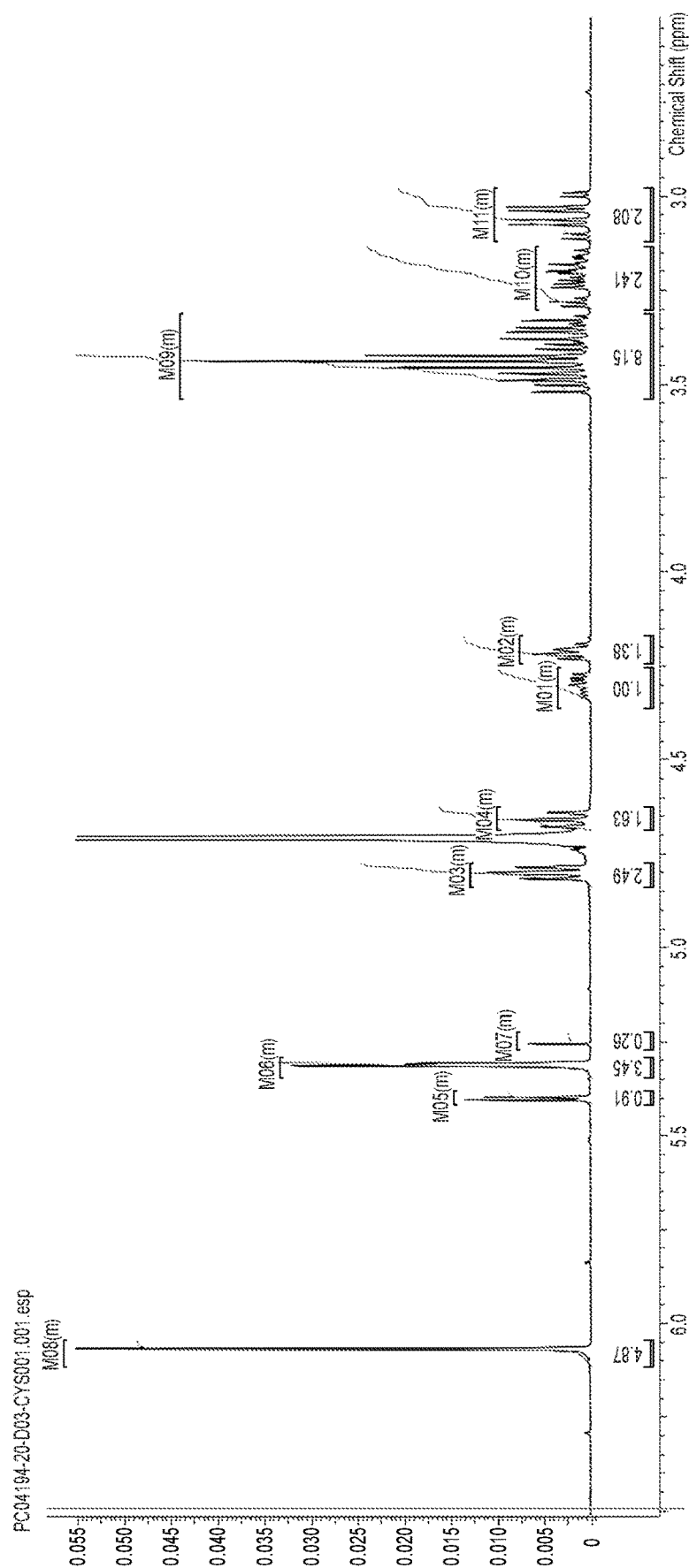
FIG. 1 is the $^1$H-NMR spectrum of the white solid in example 2.
Figure 2:
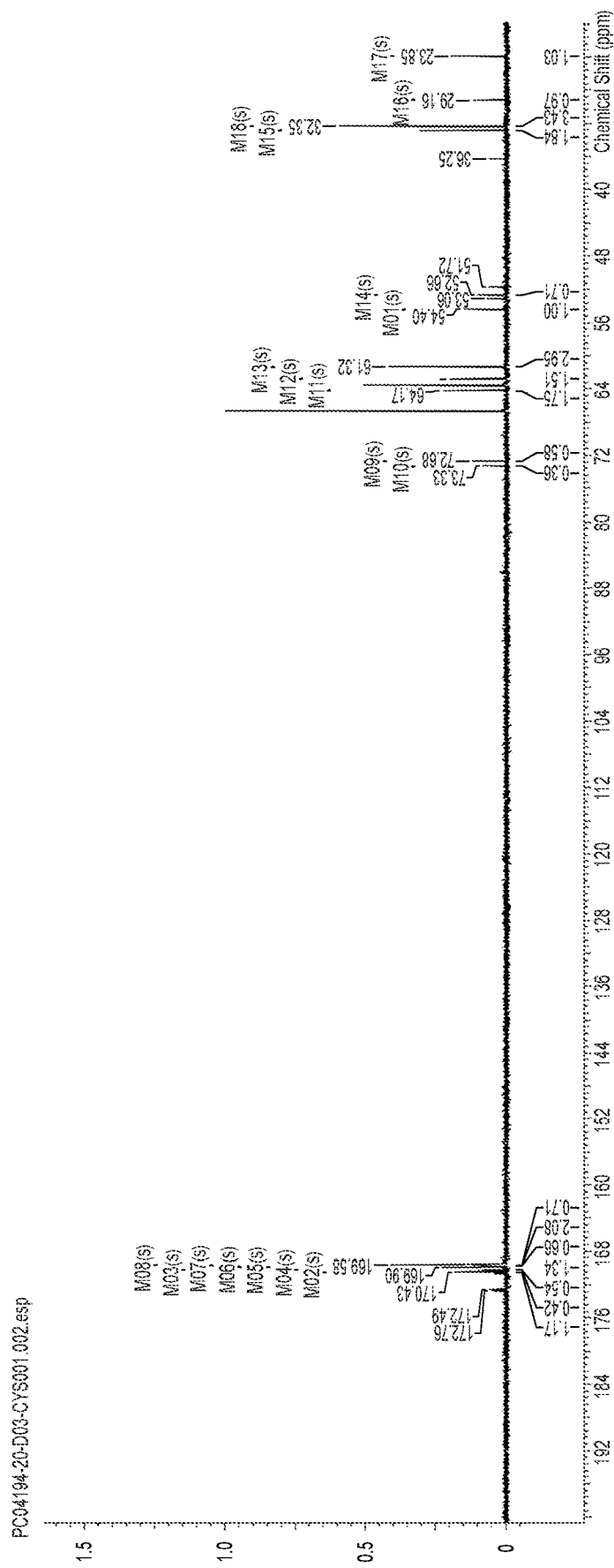
FIG. 2 is the $^{13}$C-NMR spectrum of the white solid in example 2.
Figure 3:
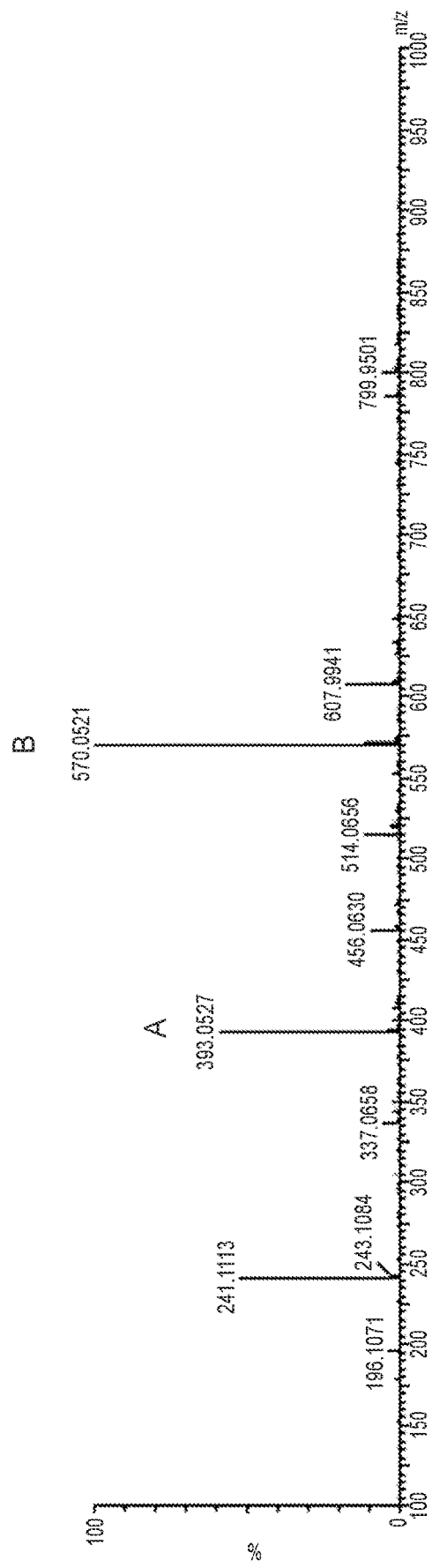
FIG. 3 is the LC-MS spectrum of the white solid in example 2.

When charging 0.1% cysteine into 10% DCA sample-01 in toluene, the inventors found that some white solid precipitated out. The white solid was filtered and dried. $^1$-NMR, $^{13}$C-NMR and LC-MS showed that the main impurity was the condensate of glyoxylic acid with cysteine (Compounds A and B). Results of structure identification information were shown in FIG. 1, FIG. 2 and FIG. 3.

A

Calc. for 392.9823, Observe 393.0527.

B

Calc. for 569.9919, Observe 570.0521.

Figure 4:
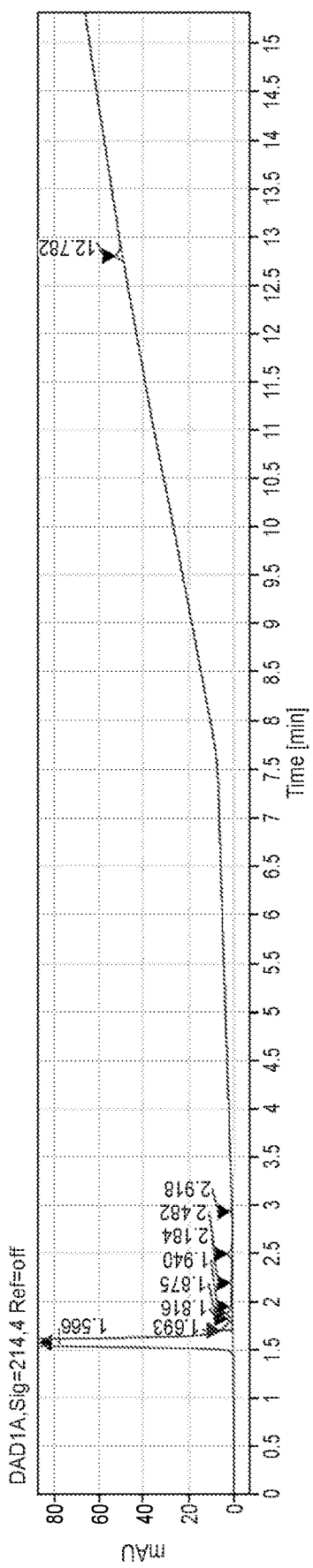
FIG. 4 is the HPLC spectrum of GA standard substance.
Figure 5:
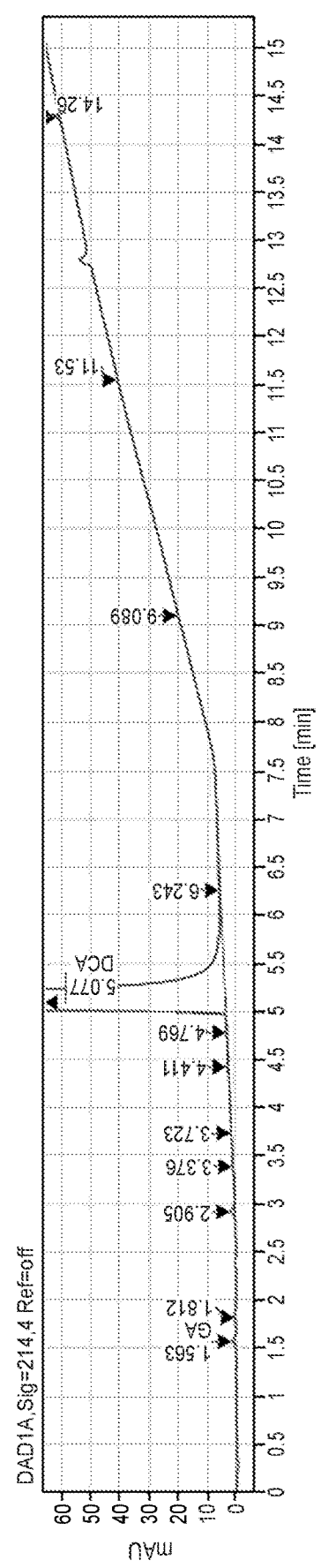
FIG. 5 is the HPLC spectrum of the DCA sample-01.

0.058% of glyoxylic acid in the DCA sample-01 was observed by HPLC method. In the HPLC method, STD is glyoxylic acid monohydrate (Source: Aladdin; Lot #F1714025). The HPLC spectra of GA and the DCA sample-01 are as shown in FIG. 4 and FIG. 5.

Example 3: Preparation and Detection of DCA Reagents 3.1. Preparation of DCA reagents To 500 g DCA sample-01 was charged 5 g of capture reagents (1% w/w or 1% v/v) including cysteine, lysine, phenylalanine (amino acids), (2R)-propane-1,2-diol (difunctional groups chemicals), hydroxylamine hydrochloride, triethylsilane (reductants) etc. The mixtures were incubated (e.g., stood or stirred) for 12-36 hrs, then vacuum distillation was conducted to obtain DCA reagents.

3.2. Detection of DCA reagents 3.2.1. Samples preparation (4 mg/mL DCA reagents)

About 200 mg of samples were accurately weighed and added into different 50 mL volumetric flasks, then diluted to volume with diluent (i.e. water), and mixed well.

Note: Samples referred to DCA reagents.

3.2.2. STD preparation (0.01 μg/mL of GA)

3.2.2.1. About 31 mg of GA.H$_2$O (Aladin; Lot #F1714025) was accurately weighed and added into a 25 mL volumetric flask, then diluted to volume with diluent (i.e. water), and mixed well, labeled as GA-1.

3.2.2.2. 200 μL of GA-1 was accurately removed into a 100 mL volumetric flask, then diluted to volume with diluent (i.e. water), and mixed well, labeled as GA-2.

3.2.2.3. 0.5 mL of GA-2 was accurately removed into a 100 mL volumetric flask, then diluted to volume with diluent (i.e. water), and mixed well, labeled as GA-3 (0.01 μg/mL of GA).

3.2.3. IC detection
Instrument: ICS-6000;
Column Dionex IonPac AS18, 4×250 mm;
Mobile phase: KOH (RFC):20 mM aqueous solution (RFC: Reagent free controller);
Flow rate: 1.0 mL/min;
Aers-4 mm Suppressor: 50 mA;
Injection volume: 25 µL;
Analysis time: 20 min.
3.3. Results: The results were summarized in Table 2.

TABLE 2

| DCA samples | Capture reagents | Content | Glyoxylic acid in the DCA reagents |
|---|---|---|---|
| DCA reagent 1 | Cysteine | 1% (w/w) | 1.65 ppm |
| DCA reagent 2 | Lysine | 1% (w/w) | 1.04 ppm |
| DCA reagent 3 | Phenylalanine | 1% (w/w) | 1.5 ppm |
| DCA reagent 4 | (2R)-propane-1,2-diol | 1% (v/v) | 304 ppm |
| DCA reagent 5 | Hydroxylamine hydrochloride | 1% (v/v) | 50.75 ppm |
| DCA reagent 6 | Triethylsilane | 1% (v/v) | 1.01 ppm |
| DCA sample-01 | — | — | 2142.7 ppm |

Conclusions:
The content of glyoxylic acid in the DCA reagent was less than 2.5 ppm when choosing cysteine, lysine, triethylsilane or phenylalanine as capture reagents. And when choosing other capture reagents, glyoxylic acid in the DCA sample-01 was also effectively decreased.

The detection method of the present disclosure can be used to detect the content of glyoxylic acid in DCA samples.

Example 4: Evaluation of Glyoxylic Acid in DCA Reagents 4.1. Samples preparation (4 mg/mL DCA reagents)
The preparation method was the same as section 3.2.1.
4.2. STD preparation (0.01 µg/mL of GA)
The preparation method was the same as section 3.2.2.
4.3. Specification of residual GA: X (X is the content of glyoxylic acid in DCA sample which does not have effect on oligonucleotide synthesis according to actual needs, in the example, X is 2.5 ppm)
4.4. Report results (limit method):
Compare STD and sample chromatogram with blank chromatogram, and integrate GA peak in STD solution and sample solution, compare their peak areas.
If the peak area of GA in sample injection is more than that in standard solution, report the result as ">X ppm".
If the peak area of GA in sample injection is equal to that in standard solution, report the result as "=X ppm".
If the peak area of GA in sample injection is less than that in standard solution, report the result as " <X ppm".

TABLE 3

| No. | Area (µs*min) | Report results |
|---|---|---|
| STD | 0.000296 | / |
| DCA reagent 1 | 0.000286 | <2.5 ppm |
| DCA reagent 2 | 0.000214 | <2.5 ppm |
| DCA reagent 3 | 0.000189 | <2.5 ppm |
| DCA reagent 4 | 0.034351 | >2.5 ppm |
| DCA reagent 5 | 0.008913 | >2.5 ppm |
| DCA reagent 6 | 0.000271 | <2.5 ppm |

Specification of residual GA may be set according to actual needs.

Conclusions:
The evaluation method of the present disclosure can be used to detect whether the content of glyoxylic acid in the DCA samples meets specific requirements.

Example 5: Oligonucleotide Synthesis 5.1. Synthesis of oligodeoxyribonucleotide T10 (TTTTT TTTTT)
Oligodeoxyribonucleotide T10 was synthesized using standard phosphoramidite chemistry at 0.1 mmol scale on polystyrene primer dT 350 support using an automated AKTA OP100 Synthesizer with 6.3 mL reaction column.

For each amidite assembly, four chemical reactions were conducted including detrilyation, coupling, oxidization and capping.

The detritlyation was conducted using 10% DCA reagents (see table 4) in toluene (v/v) with UV 350 nm monitoring control. The coupling recycle consists of co-delivery of 2.0 equivalents of 0.2M amidites solution in acetonitrile and 0.6 M ETT in acetonitrile in a 2:3 flow ratio over the course of 0.5 minutes, recirculation through the column for 4 min, oxidation with 0.05 M iodine in 9:1 pyridine:water (v/v), capping with 0.5 CV of a capping mixture (1:1, v/v) of acetic anhydride acetonitrile (1:4, v/v) and N-methylimidazole-pyridine-acetonitrile (2:3:5, v/v/v) in 0.5 min, and washing with acetonitrile at each block.

T10 was cleaved from the solid support with concomitant removal of nucleoside protecting groups by addition of a 1:1 mixture of 40 wt % methylamine aqueous solution and ammonium hydroxide aqueous solution (10 mL per gram of synthesized oligonucleotide) to the support and the resulting mixture was incubated at 30-40° C. for 2-3 hrs in a shaker.

The mixture was filtered through glass fiber filter, wash the support with purified water, and combine the filtrate. Take sample for analysis by MS and HPLC after adjusting the pH to 7.0-9.0 by 20% acetic acid.

5.2. Synthesis of Oligodeoxyribonucleotide 17mer (CCCGGGTTTCGTCGTAA)
Oligodeoxyribonucleotide 17mer DMT-CCCGGGTTTCGTCGTAA was synthesized using standard phosphoramidite chemistry at 0.2 mmol scale on PS Primer Unylinker350 support using an automated AKTA OP100 Synthesizer with 6.3 mL reaction column.

For each amidites assembly, four chemical reactions were conducted including detrilyation, coupling, oxidization and capping.

The detritlyation was conducted using 10% DCA reagents (see table 4) in toluene (v/v) with UV 350 nm monitoring control. The coupling recycle consists of co-delivery of 2.0 equivalents of 0.2M amidites solution in acetonitrile and 0.6M ETT in acetonitrile in a 2:3 flow ratio over the course of 0.5 minute, recirculation through the column for 4 minutes, oxidation with 0.05M iodine in 9:1 pyridine:water (v/v), capping with 0.5 CV of a capping mixture (1:1, v/v) of acetic anhydride acetonitrile (1:4, v/v) and N-methylimi-dazole-pyridine-acetonitrile (2:3:5, v/v/v) in 0.5 min in 0.5 minute, and washing with acetonitrile at each block.

17 mer was cleaved from the solid support with concomitant removal of nucleoside protecting groups by addition ammonium hydroxide aqueous solution (10 mL per gram of synthesized oligonucleotide) to the support and the resulting mixture was incubated at 50-60° C. for 15-17 hrs in a shaker.

The mixture was filtered through glass fiber filter, wash the support with purified water, and combine the filtrate. Take sample for analysis by MS and HPLC.

TABLE 4

| Samples | DNA sequence | Glyoxylic acid content (ppm) | DCA Purity (HPLC) |
|---|---|---|---|
| DCA reagent 7 | TTTTT TTTTT (SEQ ID NO: 1) | N/A | 95.52% |
| DCA reagent 8 | TTTTT TTTTT (SEQ ID NO: 1) | 2.5 ppm | 94.58% |
| DCA reagent 9 | TTTTT TTTTT (SEQ ID NO: 1) | 6.0 ppm | 93.24% |
| DCA reagent 10 | TTTTT TTTTT (SEQ ID NO: 1) | 12.0 ppm | 92.68% |
| DCA reagent 8 | CCCGGGTTTCGTCGTAA (SEQ ID NO: 2) | 2.5 ppm | 86.42% |
| DCA reagent 9 | CCCGGGTTTCGTCGTAA (SEQ ID NO: 2) | 6.0 ppm | 79.71% |

5.3. Preparation of DCA reagents

DCA reagent 7:

To 500 g DCA sample-01 was charged much excessive amount of cysteine. The mixtures were stood for 16 hrs, then vacuum distillation was conducted to obtain DCA reagent 7, which was detected by using the method as described in section 3.2 in example 3, and no GA was detected (N/A).

DCA reagent 8

To 500 g DCA sample-01 was charged 2.5 g of cysteine. The mixtures were stood for 16 hrs, then vacuum distillation was conducted to obtain a DCA reagent 8, which was detected by using the method as described in section 3.2 in example 3, and the content of GA was 2.5 ppm.

DCA reagent 9 & DCA reagent 10:

To 50 g of DCA reagent 7 was charged 0.5 g glyoxylic acid and the mixture was incubated under 25-50° C. for 0.5 hrs. Then the mixture was filtered to get a DCA sample-03 containing 7200 ppm glyoxylic acid. The DCA sample-03 with 7200 ppm glyoxylic acid was diluted with DCA for 1200 times and 600 times to get DCA reagent 9 and DCA reagent 10.

Conclusions:

After treating with capture reagents of the present disclosure and vacuum distillation, the DCA sample-01 could also be used for oligonucleotide synthesis. Therefore, glyoxylic acid is an impurity in commercially available DCA products, which may cause the oligonucleotide synthesis failure.

It is to be understood that the foregoing description of preferred examples is intended to be purely illustrative of the principles of the disclosure, rather than exhaustive thereof, and that changes and variations will be apparent to those skilled in the art, and that the present disclosure is not intended to be limited other than expressly set forth in the following claims.

What is claimed is:

1. A process for preparing a dichloroacetic acid composition having less than 1000 ppm glyoxylic acid, comprising: mixing a dichloroacetic acid material having greater than 1000 ppm glyoxylic acid with a glyoxylic acid capture reagent to obtain the dichloroacetic acid composition having less than 1000 ppm glyoxylic acid.

2. The process as defined in claim 1, wherein the capture reagent is selected from amino acids, chemicals having bifunctional or multifunctional groups, hydroxylamine compounds, reductants, and mixtures thereof.

3. The process as defined in claim 2, wherein
1) the amino acids are selected from cysteine, lysine and phenylalanine, or mixtures thereof;
2) the chemicals having bifunctional or multifunctional groups are selected from dihydric alcohols;
3) the hydroxylamine compounds are selected from hydroxylamine hydrochloride, and/or,
4) the reductants are selected from silanes.

4. The process as defined in claim 1, further comprising distillation of the dichloroacetic acid after mixing the dichloroacetic acid material and the capture reagent.

5. A method of synthesizing an oligonucleotide, comprising:
a) preparing or having prepared a substantially pure dichloroacetic acid having less than 50 ppm glyoxylic acid; and
b) mixing the substantially pure dichloroacetic acid with a protected oligonucleotide having an acid labile protecting group under conditions suitable to remove the acid labile protecting group, thereby producing a deprotected oligonucleotide
wherein the substantially pure dichloroacetic acid is prepared from a starting dichloroacetic acid composition having glyoxylic acid by reducing the level of glyoxylic acid to less than 50 ppm.

6. The method of claim 5, wherein prior to the mixing, the substantially pure dichloroacetic acid is determined to comprise less than 50 ppm glyoxylic acid.

7. The method of claim 5, wherein prior to the mixing, the substantially pure dichloroacetic acid is determined to comprise less than 50 ppm glyoxylic acid by ion chromatography.

8. The method of claim 5, wherein the substantially pure dichloroacetic acid is prepared from reacting the starting dichloroacetic acid composition with a glyoxylic acid capture reagent to reduce the level of glyoxylic acid to less than 50 ppm.

9. The method of claim 5, wherein the protected oligonucleotide comprises a 5'-hydroxyl protected with the acid labile protecting group.

10. The method of claim 5, wherein the acid labile protecting group is a trityl group.

11. The method of claim 5, wherein the protected oligonucleotide is bound to a solid support.

12. A method of synthesizing an oligonucleotide, the method comprising:
a) determining or having determined a substantially pure dichloroacetic acid as having less than 50 ppm glyoxylic acid; and
b) mixing the substantially pure dichloroacetic acid with a protected oligonucleotide having an acid labile protecting group under conditions suitable to remove the acid labile protecting group, thereby producing a deprotected oligonucleotide.

13. The method of claim 12, comprising determining or having determined the substantially pure dichloroacetic acid as having less than 50 ppm glyoxylic acid by ion chromatography.

14. The method of claim 12, wherein the protected oligonucleotide comprises a 5'-hydroxyl protected with the acid labile protecting group.

15. The method of claim 12, wherein the acid labile protecting group is a trityl group.

16. The method of claim 12, wherein the protected oligonucleotide is bound to a solid support.

17. A method of producing a dichloroacetic acid composition, comprising 1) analyzing the level of glyoxylic acid in a starting dichloroacetic acid composition; and 2) reducing the level of glyoxylic acid in the starting dichloroacetic acid composition to be less than 50 ppm by mixing the starting dichloroacetic acid composition with a glyoxylic acid capture agent, thereby producing the dichloroacetic acid composition.

18. The process as defined in claim 17, wherein the capture reagent is selected from amino acids, chemicals having bifunctional or multifunctional groups, hydroxylamine compounds, reductants, and mixtures thereof.

19. The process as defined in claim 18, wherein
1) the amino acids are selected from cysteine, lysine and phenylalanine, or mixtures thereof;
2) the chemicals having bifunctional or multifunctional groups are selected from dihydric alcohols;
3) the hydroxylamine compounds are selected from hydroxylamine hydrochloride, and/or,
4) the reductants are selected from silanes.

20. The process as defined in claim 17, further comprising distillation of the dichloroacetic acid after mixing the starting dichloroacetic acid composition and the glyoxylic acid capture reagent.

* * * * *

SEQUENCE LISTING

```
Sequence total quantity: 2
SEQ ID NO: 1            moltype = DNA  length = 10
FEATURE                 Location/Qualifiers
misc_feature            1..10
                        note = Synthetic polynucleotide
source                  1..10
                        mol_type = other DNA
                        organism = synthetic construct
SEQUENCE: 1
tttttttttt                                                                 10

SEQ ID NO: 2            moltype = DNA  length = 17
FEATURE                 Location/Qualifiers
misc_feature            1..17
                        note = Synthetic polynucleotide
source                  1..17
                        mol_type = other DNA
                        organism = synthetic construct
SEQUENCE: 2
cccgggtttc gtcgtaa                                                         17
```